US008209051B2

(12) United States Patent
Wang et al.

(10) Patent No.: US 8,209,051 B2
(45) Date of Patent: Jun. 26, 2012

(54) MEDICAL TELE-ROBOTIC SYSTEM

(75) Inventors: Yulun Wang, Goleta, CA (US); Keith Phillip Laby, Santa Barbara, CA (US); Charles S. Jordan, Santa Barbara, CA (US); Steven Edward Butner, Goleta, CA (US); Jonathan Southard, Santa Barbara, CA (US)

(73) Assignee: Intouch Technologies, Inc., Goleta, CA (US)

( * ) Notice: Subject to any disclaimer, the term of this patent is extended or adjusted under 35 U.S.C. 154(b) by 325 days.

(21) Appl. No.: 11/529,108

(22) Filed: Sep. 27, 2006

(65) Prior Publication Data

US 2007/0021871 A1 Jan. 25, 2007

Related U.S. Application Data

(62) Division of application No. 10/206,457, filed on Jul. 25, 2002, now Pat. No. 6,925,357, and a division of application No. 10/913,621, filed on Aug. 6, 2004, now Pat. No. 7,164,970.

(51) Int. Cl.
*G06F 19/00* (2011.01)

(52) U.S. Cl. ........ 700/245; 700/231; 700/233; 700/235; 700/242; 700/243; 318/568.11; 318/568.12; 318/568.13; 318/568.21; 318/568.25; 600/117; 600/118; 600/407; 600/426; 600/429; 606/1; 606/102; 606/130; 606/139; 901/1; 901/2; 901/27

(58) Field of Classification Search .................. 700/231, 700/233, 235, 242, 243, 244, 245; 318/568.11, 318/568.12, 568.13, 568.16, 568.21, 568.25; 600/117, 118, 407, 426, 429, 587, 595; 606/1, 606/102, 130, 139; 901/1, 2, 27

See application file for complete search history.

(56) References Cited

U.S. PATENT DOCUMENTS

| 3,821,995 | A | 7/1974 | Aghnides |
| 4,413,693 | A | 11/1983 | Derby |
| 4,471,354 | A | 9/1984 | Smith |
| 4,519,466 | A | 5/1985 | Shiraishi |
| 4,638,445 | A | 1/1987 | Mattaboni |

(Continued)

FOREIGN PATENT DOCUMENTS

CA 2289697 A1 5/1998

(Continued)

OTHER PUBLICATIONS

Thrun et al., Probabilistic Algorithms and the Interactive Museum Tour-Guide Robot Minerva, Internet, p. 1-35.*

(Continued)

*Primary Examiner* — James Trammell
*Assistant Examiner* — McDieunel Marc
(74) *Attorney, Agent, or Firm* — Paul Evans

(57) ABSTRACT

A robotic system that includes a remote controlled robot. The robot may include a camera, a monitor and a holonomic platform all attached to a robot housing. The robot may be controlled by a remote control station that also has a camera and a monitor. The remote control station may be linked to a base station that is wirelessly coupled to the robot. The cameras and monitors allow a care giver at the remote location to monitor and care for a patient through the robot. The holonomic platform allows the robot to move about a home or facility to locate and/or follow a patient.

3 Claims, 11 Drawing Sheets

U.S. PATENT DOCUMENTS

| | | | |
|---|---|---|---|
| 4,669,168 A | 6/1987 | Tamura et al. | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,777,416 A | 10/1988 | George et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,942,538 A | 7/1990 | Yuan et al. | |
| 4,974,607 A | 12/1990 | Miwa | |
| 4,977,971 A | 12/1990 | Crane et al. | |
| 5,006,988 A | 4/1991 | Borenstein et al. | |
| 5,040,116 A | 8/1991 | Evans, Jr. et al. | |
| 5,051,906 A | 9/1991 | Evans, Jr. et al. | |
| 5,073,749 A | 12/1991 | Kanayama | |
| 5,084,828 A | 1/1992 | Kaufman et al. | |
| 5,130,794 A | 7/1992 | Ritchey | |
| 5,153,833 A | 10/1992 | Gordon et al. | |
| 5,157,491 A | 10/1992 | Kassatly | |
| 5,186,270 A | 2/1993 | West | |
| 5,193,143 A | 3/1993 | Kaemmerer et al. | |
| 5,217,453 A | 6/1993 | Wilk | |
| 5,224,157 A | 6/1993 | Yamada et al. | |
| 5,231,693 A | 7/1993 | Backes et al. | |
| 5,236,432 A | 8/1993 | Matsen, III et al. | |
| 5,305,427 A | 4/1994 | Nagata | |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,350,033 A | 9/1994 | Kraft | |
| 5,366,896 A | 11/1994 | Margrey et al. | |
| 5,374,879 A | 12/1994 | Pin et al. | |
| 5,417,210 A * | 5/1995 | Funda et al. | 600/425 |
| 5,419,008 A | 5/1995 | West | |
| 5,436,542 A | 7/1995 | Petelin et al. | |
| 5,441,047 A | 8/1995 | David | |
| 5,442,728 A * | 8/1995 | Kaufman et al. | 704/270 |
| 5,462,051 A | 10/1995 | Oka | |
| 5,486,853 A | 1/1996 | Baxter et al. | |
| 5,510,832 A | 4/1996 | Garcia | |
| 5,539,741 A | 7/1996 | Barraclough et al. | |
| 5,544,649 A | 8/1996 | David et al. | |
| 5,553,609 A | 9/1996 | Chen et al. | |
| 5,572,229 A | 11/1996 | Fisher | |
| 5,572,999 A * | 11/1996 | Funda et al. | 600/118 |
| 5,630,566 A | 5/1997 | Case | |
| 5,636,218 A | 6/1997 | Ishikawa et al. | |
| 5,652,849 A | 7/1997 | Conway et al. | |
| 5,684,695 A | 11/1997 | Bauer | |
| 5,701,904 A | 12/1997 | Simmons et al. | |
| 5,749,058 A | 5/1998 | Hashimoto | |
| 5,749,362 A * | 5/1998 | Funda et al. | 600/407 |
| 5,754,631 A | 5/1998 | Cave | |
| 5,762,458 A | 6/1998 | Wang et al. | |
| 5,786,846 A | 7/1998 | Hiroaki | |
| 5,802,494 A * | 9/1998 | Kuno | 705/2 |
| 5,836,872 A | 11/1998 | Kenet et al. | |
| 5,838,575 A | 11/1998 | Lion | |
| 5,857,534 A | 1/1999 | DeVault et al. | |
| 5,867,653 A | 2/1999 | Aras et al. | |
| 5,871,451 A | 2/1999 | Unger et al. | |
| 5,876,325 A | 3/1999 | Mizuno et al. | |
| 5,911,036 A | 6/1999 | Wright et al. | |
| 5,917,958 A | 6/1999 | Nunally et al. | |
| 5,927,423 A | 7/1999 | Wada et al. | |
| 5,954,692 A | 9/1999 | Smith et al. | |
| 5,959,423 A | 9/1999 | Nakanishi et al. | |
| 5,966,130 A | 10/1999 | Benman, Jr. | |
| 5,974,446 A | 10/1999 | Sonnenreich et al. | |
| 6,006,946 A | 12/1999 | Williams et al. | |
| 6,036,812 A | 3/2000 | Williams et al. | |
| 6,133,944 A | 10/2000 | Braun et al. | |
| 6,135,228 A | 10/2000 | Asada et al. | |
| 6,148,100 A | 11/2000 | Anderson et al. | |
| 6,170,929 B1 | 1/2001 | Wilson et al. | |
| 6,175,779 B1 | 1/2001 | Barrett | |
| 6,201,984 B1 * | 3/2001 | Funda et al. | 600/407 |
| 6,211,903 B1 | 4/2001 | Bullister | |
| 6,219,587 B1 * | 4/2001 | Ahlin et al. | 700/233 |
| 6,232,735 B1 | 5/2001 | Baba et al. | |
| 6,233,504 B1 | 5/2001 | Das et al. | |
| 6,233,735 B1 | 5/2001 | Ebihara | |
| 6,256,556 B1 | 7/2001 | Zenke | |
| 6,259,806 B1 | 7/2001 | Green | |
| 6,259,956 B1 | 7/2001 | Myers et al. | |
| 6,266,162 B1 | 7/2001 | Okamura et al. | |
| 6,266,577 B1 | 7/2001 | Popp et al. | |
| 6,289,263 B1 | 9/2001 | Mukherjee | |
| 6,292,713 B1 | 9/2001 | Jouppi et al. | |
| 6,304,050 B1 | 10/2001 | Skaar et al. | |
| 6,321,137 B1 | 11/2001 | De Smet | |
| 6,325,756 B1 | 12/2001 | Webb et al. | |
| 6,327,516 B1 | 12/2001 | Zenke | |
| 6,330,486 B1 | 12/2001 | Padula | |
| 6,330,493 B1 | 12/2001 | Takahashi et al. | |
| 6,346,950 B1 | 2/2002 | Jouppi | |
| 6,369,847 B1 | 4/2002 | James et al. | |
| 6,381,515 B1 * | 4/2002 | Inoue et al. | 700/245 |
| 6,408,230 B2 | 6/2002 | Wada | |
| 6,430,471 B1 | 8/2002 | Kintou et al. | |
| 6,430,475 B2 | 8/2002 | Okamoto | |
| 6,438,457 B1 | 8/2002 | Yokoo et al. | |
| 6,452,915 B1 | 9/2002 | Jorgensen | |
| 6,457,043 B1 * | 9/2002 | Kwak et al. | 709/204 |
| 6,463,361 B1 | 10/2002 | Wang et al. | |
| 6,466,844 B1 | 10/2002 | Ikeda et al. | |
| 6,468,265 B1 | 10/2002 | Evans et al. | |
| 6,474,434 B1 | 11/2002 | Bech | |
| 6,480,762 B1 | 11/2002 | Uchikubo et al. | |
| 6,491,701 B2 | 12/2002 | Tierney et al. | |
| 6,496,099 B2 | 12/2002 | Wang et al. | |
| 6,496,755 B2 | 12/2002 | Wallach et al. | |
| 6,501,740 B1 | 12/2002 | Sun et al. | |
| 6,507,773 B2 | 1/2003 | Parker et al. | |
| 6,522,906 B1 | 2/2003 | Salisbury et al. | |
| 6,523,629 B1 | 2/2003 | Buttz et al. | |
| 6,526,332 B2 | 2/2003 | Sakamoto et al. | |
| 6,529,802 B1 | 3/2003 | Kawakita et al. | |
| 6,532,404 B2 | 3/2003 | Colens | |
| 6,535,182 B2 | 3/2003 | Stanton | |
| 6,535,793 B2 | 3/2003 | Allard | |
| 6,540,039 B1 | 4/2003 | Yu | |
| 6,543,899 B2 | 4/2003 | Covannon et al. | |
| 6,549,215 B2 | 4/2003 | Jouppi | |
| 6,563,533 B1 | 5/2003 | Colby | |
| 6,580,246 B2 | 6/2003 | Jacobs | |
| 6,581,798 B2 | 6/2003 | Liff et al. | |
| 6,587,750 B2 | 7/2003 | Gerbi et al. | |
| 6,594,269 B1 | 7/2003 | Polcyn | |
| 6,594,552 B1 | 7/2003 | Nowlin et al. | |
| 6,604,019 B2 * | 8/2003 | Ahlin et al. | 700/231 |
| 6,604,021 B2 | 8/2003 | Imai et al. | |
| 6,611,120 B2 | 8/2003 | Song et al. | |
| 6,646,677 B2 | 11/2003 | Noro et al. | |
| 6,650,748 B1 | 11/2003 | Edwards et al. | |
| 6,666,374 B1 | 12/2003 | Green et al. | |
| 6,684,129 B2 | 1/2004 | Salisbury et al. | |
| 6,691,000 B2 | 2/2004 | Nagai et al. | |
| 6,710,797 B1 | 3/2004 | McNelley et al. | |
| 6,728,599 B2 * | 4/2004 | Wang et al. | 700/258 |
| 6,764,373 B1 | 7/2004 | Osawa et al. | |
| 6,769,771 B2 * | 8/2004 | Trumbull | 352/243 |
| 6,781,606 B2 | 8/2004 | Jouppi et al. | |
| 6,784,916 B2 | 8/2004 | Smith | |
| 6,785,589 B2 | 8/2004 | Eggenberger et al. | |
| 6,791,550 B2 * | 9/2004 | Goldhor et al. | 345/475 |
| 6,799,065 B1 | 9/2004 | Niemeyer | |
| 6,799,088 B2 | 9/2004 | Wang et al. | |
| 6,804,580 B1 | 10/2004 | Stoddard et al. | |
| 6,804,656 B1 | 10/2004 | Rosenfeld et al. | |
| 6,810,411 B1 * | 10/2004 | Coughlin et al. | 709/203 |
| 6,836,703 B2 | 12/2004 | Wang et al. | |
| 6,839,612 B2 | 1/2005 | Sanchez et al. | |
| 6,840,904 B2 | 1/2005 | Goldberg | |

| | | |
|---|---|---|
| 6,845,297 B2 | 1/2005 | Allard |
| 6,852,107 B2 | 2/2005 | Wang et al. |
| 6,853,878 B2 | 2/2005 | Hirayama et al. |
| 6,871,117 B2 | 3/2005 | Wang et al. |
| 6,879,879 B2 | 4/2005 | Jouppi et al. |
| 6,892,112 B2 | 5/2005 | Wang et al. |
| 6,895,305 B2 | 5/2005 | Lathan et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,965,394 B2 | 11/2005 | Gutta et al. |
| 6,995,664 B1 | 2/2006 | Darling |
| 7,058,689 B2 * | 6/2006 | Parker et al. ............... 709/206 |
| 7,092,001 B2 * | 8/2006 | Schulz ..................... 348/14.05 |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,991 B2 | 10/2006 | Graf et al. |
| 7,127,325 B2 | 10/2006 | Nagata et al. |
| 7,129,970 B2 * | 10/2006 | James et al. ............... 348/14.01 |
| 7,142,945 B2 | 11/2006 | Wang et al. |
| 7,142,947 B2 | 11/2006 | Wang et al. |
| 7,151,982 B2 * | 12/2006 | Liff et al. .................... 700/241 |
| 7,154,526 B2 | 12/2006 | Foote et al. |
| 7,155,306 B2 * | 12/2006 | Haitin et al. ............... 700/242 |
| 7,156,809 B2 | 1/2007 | Quy |
| 7,158,859 B2 | 1/2007 | Wang et al. |
| 7,158,860 B2 | 1/2007 | Wang et al. |
| 7,161,322 B2 | 1/2007 | Wang et al. |
| 7,164,969 B2 | 1/2007 | Wang et al. |
| 7,174,238 B1 | 2/2007 | Zweig |
| 7,184,559 B2 | 2/2007 | Jouppi |
| 7,188,000 B2 | 3/2007 | Chiappetta et al. |
| 7,206,627 B2 | 4/2007 | Abovitz et al. |
| 7,215,786 B2 | 5/2007 | Nakadai et al. |
| 7,256,708 B2 | 8/2007 | Rosenfeld |
| 7,262,573 B2 | 8/2007 | Wang et al. |
| 7,346,429 B2 | 3/2008 | Goldenberg et al. |
| 7,382,399 B1 | 6/2008 | McCall et al. |
| 7,386,730 B2 | 6/2008 | Uchikubo |
| RE42,288 E * | 4/2011 | Degioanni ................. 348/14.01 |
| 7,924,323 B2 * | 4/2011 | Walker et al. ............... 348/231.2 |
| 2001/0002448 A1 | 5/2001 | Wilson |
| 2001/0010053 A1 | 7/2001 | Ben-Shachar et al. |
| 2001/0037163 A1 | 11/2001 | Allard |
| 2001/0054071 A1 | 12/2001 | Loeb |
| 2002/0015296 A1 | 2/2002 | Howell et al. |
| 2002/0027597 A1 | 3/2002 | Sachau |
| 2002/0049517 A1 | 4/2002 | Ruffner |
| 2002/0057279 A1 | 5/2002 | Jouppi |
| 2002/0058929 A1 | 5/2002 | Green |
| 2002/0063726 A1 | 5/2002 | Jouppi |
| 2002/0095238 A1 | 7/2002 | Ahlin et al. |
| 2002/0104094 A1 | 8/2002 | Alexander et al. |
| 2002/0111988 A1 * | 8/2002 | Sato ............................ 709/202 |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2003/0030397 A1 | 2/2003 | Simmons |
| 2003/0050733 A1 | 3/2003 | Wang et al. |
| 2003/0060808 A1 | 3/2003 | Wilk |
| 2003/0135203 A1 | 7/2003 | Wang et al. |
| 2003/0144579 A1 | 7/2003 | Buss |
| 2003/0151658 A1 | 8/2003 | Smith |
| 2003/0174285 A1 * | 9/2003 | Trumbull ..................... 352/85 |
| 2003/0180697 A1 | 9/2003 | Kim et al. |
| 2004/0019406 A1 | 1/2004 | Wang et al. |
| 2004/0117065 A1 | 6/2004 | Wang et al. |
| 2004/0138547 A1 * | 7/2004 | Wang et al. .................. 600/407 |
| 2004/0143421 A1 | 7/2004 | Wang et al. |
| 2004/0162637 A1 | 8/2004 | Wang et al. |
| 2004/0167668 A1 | 8/2004 | Wang et al. |
| 2005/0021183 A1 * | 1/2005 | Wang et al. .................. 700/245 |
| 2005/0049898 A1 | 3/2005 | Hirakawa |
| 2005/0065659 A1 | 3/2005 | Tanaka |
| 2005/0071046 A1 | 3/2005 | Miyazaki et al. |
| 2005/0104964 A1 | 5/2005 | Bovyrin et al. |
| 2005/0182322 A1 | 8/2005 | Grispo |
| 2005/0267826 A1 | 12/2005 | Levy et al. |
| 2006/0047365 A1 | 3/2006 | Ghodoussi et al. |
| 2006/0052676 A1 | 3/2006 | Wang et al. |
| 2006/0161303 A1 | 7/2006 | Wang et al. |
| 2007/0273751 A1 | 11/2007 | Sachau |
| 2008/0201017 A1 | 8/2008 | Wang et al. |
| 2008/0255703 A1 | 10/2008 | Wang et al. |
| 2009/0105882 A1 | 4/2009 | Wang et al. |

FOREIGN PATENT DOCUMENTS

| | | |
|---|---|---|
| EP | 0981905 B1 | 5/1998 |
| EP | 1262142 A2 | 12/2002 |
| EP | 1573406 A2 | 9/2005 |
| EP | 1800476 A2 | 6/2007 |
| EP | 2214111 A2 | 8/2010 |
| JP | 7213753 A | 8/1995 |
| JP | 7248823 A | 9/1995 |
| JP | 07257422 A | 10/1995 |
| JP | 8084328 A | 3/1996 |
| JP | 8320727 A | 12/1996 |
| JP | 9267276 A | 10/1997 |
| JP | 10079097 A | 3/1998 |
| JP | 10288689 A | 10/1998 |
| JP | 2000-032319 A | 1/2000 |
| JP | 049800 A | 2/2000 |
| JP | 079587 A | 3/2000 |
| JP | 196876 A | 7/2000 |
| JP | 2002-046088 | 8/2000 |
| JP | 2002305743 A | 4/2001 |
| JP | 125641 A | 5/2001 |
| JP | 147718 A | 5/2001 |
| JP | 179663 A | 7/2001 |
| JP | 198865 A | 7/2001 |
| JP | 198868 A | 7/2001 |
| JP | 199356 A | 7/2001 |
| JP | 000574 A | 1/2002 |
| JP | 046088 A | 2/2002 |
| JP | 355779 A | 12/2002 |
| JP | 524824 T | 8/2004 |
| JP | 028066 A | 2/2005 |
| WO | WO 93/06690 A1 | 4/1993 |
| WO | WO 98/51078 A1 | 11/1998 |
| WO | WO99/67067 | 12/1999 |
| WO | WO 00/33726 | 6/2000 |
| WO | WO 03/077745 | 9/2003 |
| WO | WO 2006/044847 | 4/2006 |

OTHER PUBLICATIONS

Blackwell, A Wireless LAN Killer App?, 2002, Internet, p. 1-3.*
Cheetham et al., Interface Development for a Child'S Video Conferencing Robot, 2000, p. 1-4.*
Lee et al. A novel method of surgical instruction: International telementoring, 1998, Interenet, p. 1-4.*
Celi et al., "The eICU: It's not just telemedicine", Critical Care Medicine, vol. 29, No. 8 (Supplement), Aug. 2001.
Cleary et al., "State of the art in surgical robotics: Clinical applications and technology challenges", 2002 Internet, pp. 1-26.
Davies, "Robotics in Minimally Invasive Surgery", 1995, Internet, pp. 5/1-5/2.
Elhajj et al., "Supermedia in Internet-based telerobotic operations", 2001, Internet, p. 1-14.
Goldman, Lea, "Machine Dreams", Entrepreneurs, Forbes, May 27, 2002.
Gump, Michael D., "Robot Technology Improves VA Pharmacies", 2001, Internet, pp. 1-3.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
Ishihara, Ken et al., "Intelligent Microrobot DDS (Drug Delivery System) Measured and Controlled by Ultrasonics", 1991, IEEE/RSJ, pp. 1145-1150, vol. 2.

Kanehiro, Fumio et al., Virtual Humanoid Robot Platform to Develop Controllers of Real Humanoid Robots without Porting, 2001,IEEE, pp. 3217-3276.
Lim, Hun-ok et al., Control to Realize Human-like Walking of a Biped Humanoid Robot, IEE 2000, pp. 3271-3276.
Loeb, Gerald, "Virtual Visit: Improving Communication for Those Who Need It Most", 2001.
Mack, "Minimally invasive and robotic surgery", 2001, Internet IEEE, pp. 568-572.
Magne Charge—Smart Power for Electric Vehicles, Internet, Jun. 27, 2002.
McCardle et al., "The challenge of utilizing new technology in design education", 2000 Internet, pp. 122-127.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, Eric John, "Personal Tele-Embodiment", 2001.
Paulos, et al. , "Ubiquitous Tele-embodiment: Applications and Implications", International Journal of Human Computer Studies, Jun. 1997, vol. 46, No. 6, pp. 861-877.
Paulos, et al., "Designing Personal Tele-Embodiment", Presented at the IEEE International Conference on Robotics and Animation, Leuven, Belgium, May 20, 1998.
Pin et al., "A New Family of Omnidirectional and Holonomic Wheeled Platforms for Mobile Robots", IEEE, vol. 10, No. 4, Aug. 1994.
Robot Hardware Mobile Robotics Research Group, Edinburgh, "Mobile Robotics Research Group", 2000 Internet, pp. 1-2.
Roy et al., "Towards Personal Service Robots for the Elderly", Internet, Mar. 7, 2002.
Sandt, Frederic et al., "Perceptions for a Transport Robot in Public Environments", 1997, IROS '97.
Tendick et al., "Human-Machine Interfaces for Minimally Invasive Surgery", 1997, IEEE, pp. 2771-2776.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision.html, Mar. 5, 1996.
Adams, Chris, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.
Ando, et al., "A Multimedia Self-service Terminal with Conferencing Functions", IEEE, Jul. 5-7, 1995, pp. 357-362.
Android Amusement Corp., "What Marketing Secret . . . Renting Robots from Android Amusement Corp!", (Advertisement), 1982.
Applebome, "Planning Domesticated Robots for Tomorrow's Household", New York Times, http://www.theoldrobots.com/images17/dc17.JPG, Mar. 4, 1982, pp. 21 & 23.
Bar-Cohen, et al., "Virtual reality robotic telesurgery simulations using MEMICA haptic system", Internet, Mar. 5, 2001, 1-7.
Bartholomew "An Apothecary's Pharmacy", http://classes.bnf.fr/ema/grands/034.htm, 1230-1240.
Bauer, Jeffrey C. et al., "Service Robots in Health Care: The Evolution of Mechanical Solutions to Human Resource Problems", Jun. 2003.
Bauer, John et al., "Remote telesurgical mentoring: feasibility and efficacy", IEEE, 2000, 1-9.
Bischoff, "Design Concept and Realization of the Humanoid Service Robot Hermes", Field and Service Robotics, Springer, London, 1998, 485-492.
Breslow, Michael J. et al., "Effect of a multiple-site intensive care unit telemedicine program on clinical and economic outcome an alternative paradigm for intensivist staffing", Critical Care Med; vol. 32 No. 1, Jan. 2004, pp. 31-38.
Brooks, Rodney, "Remote Presence", Abstracts from Flesh & Machines, How Robots Will Change Us, Feb. 2002, 131-147.
CNN, "Floating 'droids' to roam space corridors of the future", Internet, Jan. 12, 2000, 1-4.

CNN.Com/technology, "Paging R.Robot: Machine helps doctors with patients", Internet, Sep. 30, 2003, 1-3.
Crowley, Susan L., "Hello to Our Future", AARP Bulletin, http://www.cs.cmu.ed/-nursebot/web/press/aarp 99_14/millennium.html, Jan. 2000.
Dalton, "Techniques for Web Telerobotics", PhD Thesis, University of Western Australia, http://telerobot.mech.uwa.edu.au/information.html, http://catalogue.library.uwa.edu.au/search, 2001, pp. 27-62.
Digiorgio, James, "Is Your Emergency Department of the 'Leading Edge'?", Internet, 2005, pp. 1-4.
Elhajj, et al., "Synchronization and Control of Supermedia Transmission Via the Internet", Proceedings of 2001 International Symposium on Intelligent Multimedia Video and Speech Processing., Hong Kong, May 2-4, 2001.
Fels, "Developing a Video-Mediated Communication System for Hospitalized Children", Telemedicine Journal, vol. 5,vol. 5, No. 2, 1999.
Fetterman, "Videoconferencing over the Internet", Internet, 2001, pp. 1-8.
Fiorini, P. et al., "Health Care Robotics: A Progress Report", IEEE International Conference on Robotics and Automation, 1997, Apr. 1997, pp. 1271-1276.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszSzraiders.odf/aol, 1995, 654-659.
Goldberg, "More Online Robots, Robots that Manipulate", Internet, Updated Aug. 2001, http://ford.ieor.berkeley.edu/ir/robots_a2.html.
Hameed, Mohammed et al., "A Review of Telemedicine", Journal of Telemedicine and Telecare, vol. 5, Supplement 1, http://jtt.rsmjournals.com/cgi/content/abstract/5/suppl_1/103, 1999.
Handley, et al., "RFC 2327—SDP:Session Description Protocol", http://www.faqs.org/rfcs/rfc2327.html, Apr. 1998.
Hanebeck, et al., "ROMAN: a mobile Robotic Assistant for Indoor Service Applications", Proceedings of the 1997 IEEE/RSJ International Conference on Intelligent Robots and Svstems, 1997.
Haule, et al., "Control Scheme for Delayed Teleoperation Tasks", Proceedings of the Pacific Rim Conference on Communications, Computer and Signal Processing, May 17, 1995.
Holmberg, "Development of a Holonomic Mobile Robot for Mobile Manipulation Tasks", International Conference on Field and Service Robotics, Pittsburgh, PA, Aug. 1999.
"Inventing the Future: 2000 Years of Discovery", Discovery Channel Canada, (VideoITranscript), Jan. 2, 2000.
Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.
"ITU-T H.323 Packet-based multimedia communications", ITU, http://www.itu.int/rec/T-REC-H.323-199802-S/en, Feb. 1998.
Ivanova, Natali, "Master's thesis: Internet Based Interface for Control of a Mobile Robot", Department of Numerical Analysis and Computer Science, 2003, 59 pages.
Jacobs, et al., "TeleRehab: Applying Telemedicine to Outpatient Physical Therapy", 2002.
Jenkins, et al., "Telehealth Advancing Nursing Practice", Nursing Outlook, vol. 49, No. 2, Mar./Apr. 2001.
Johanson, "Supporting video-mediated communication over the Internet", Chalmers University of Technology,Dept of Computer Engineering, Gothenburg, Sweden, 2003.
Jouppi, et al., "Mutually-Immersive Audio Telepresence", Audio Engineering Society Convention Paper presented at 113th Convention, Oct. 2002.
Jouppi, Norman et al., "First Steps Towards Mutually-Immersive Mobile Telepresence", CSCW, 02, New Orleans LA, Nov. 16-20, 2002.

Keller, et al., "Raven Interface Project", Fall 2001, http://upclose.lrdc.pitt.edu/people/louw_assets/Raven_Slides.pps.

Khatib, "Robots in Human Environments", Proc. International Conference on Control, Automation, Robotics, and Vision ICRACV2000, Singapore, Dec. 2000, pp. 454-457.

Lane, "Automated Aides", Newsday, http://www.cs.cum.edu/nursebot/web/press/nd4380.htm, Oct. 17, 2000.

Linebarger, John M. et al., "Concurrency Control Mechanisms for Closely Coupled Collaboration in Multithreaded Virtual Environments", Presence, Special Issue on Advances in Collaborative VEs, 2004.

Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, 950-1.

Luna, Nancy, "Robot a new face on geriatric care", OC Register, Aug. 6, 2003.

Mair, "Telepresence—The Technology. And Its Economic and Social Implications", IEEE Technology and Society, 1997.

Martin, Anya, "Days Ahead", Assisted Living Today, vol. 9, Nov./Dec. 2002, pp. 19-22.

Meng, et al., "E-Service Robot in Home Healthcare", Proceedings of the 2000 IEEE/RSJ, International Conference on Intelligent Robots and Systems, 2000, pp. 832-837.

Michaud, "Introducing Nursebot", The Boston Globe, http://www.cs.cmu.edu/nursebot/web/press/globe 3 01/index.html, Sep. 11, 2001, pp. 1-5.

Montemerlo, "Telepresence: Experiments in Next Generation Internet", CMU Robotics Institute, http://www.ri.cmu.edu/creative/archives.htm (Video/Transcript), Oct. 20, 1998.

Murphy, "Introduction to Al Robotics", A Bradford Book, 2000, 487.

Nakajima, et al., "A Multimedia Teleteaching System using an Electronic Whiteboard for Two Way Communication of Motion Videos and Chalkboards", IEEE, 1993, pp. 436-441.

"National Energy Research Scientific Computing Center, Berkeley Lab's RAGE Telepresence Robot Captures R&D100 Award", http://www.nersc.gov/news/newsroom/RAGE070202.php, Jul. 2, 2002.

"Nomad XR4000 Hardware Manual", Nomadic Technologies, Inc., Mar. 1999.

Ogata, et al., "Development of Emotional Communication Robot: WAMOEBA-2r—Experimental evaluation", IEEE, 2000, pp. 175-180.

Ogata, et al., "Emotional Communication Robot: Wamoeba-2R—Emotion Model and Evaluation Experiments", Internet, 1999, pp. 1-16.

Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper.pdf, 2000.

Paulos, "PRoP: Personal Roving Presence", ACM:CHI Proceedings of CHI '98, http://www.prop.org/papers/chi98.pdf, 1998, 6.

Paulos, "Video of PRoP 2 at Richmond Field Station", www.prop.org Printout of Home Page of Website and two-page Transcript of the audio portion of said PRoP Video, May 2001.

PCT/US2005/037347, "International Preliminary Report on Patentability and Written Opinion", Apr. 17, 2006, 7 pages.

PCT/US2005/037347A3, "International Search Report", Apr. 17, 2006, 2 pages.

Piquepaille, Roland, "Technology Trends, How new technologies are modifying your way of life", 2003, pp. 1-2.

Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.

Salemi, et al., "Milo: Personal robot platform", Internet, 2005, pp. 1-6.

Schaeffer, "Care-O-bot: A System for Assisting Elderly or Disabled Persons in Home Environments", Proceedings of AAATE-99, http://morpha.de/download/publications/IPA, 1999.

Schulz, D. et al., "Web Interfaces for Mobile Robots in Public Places", IEEE Robotics &Automation Magazine, IEEE, Service Center, Piscataway, NJ, US, vol. 7, No. 1, Mar. 1, 2000, pp. 1-9.

Shimoga, et al., "Touch and force reflection for telepresence surgery", IEEE, 1994, pp. 1049-1050.

Siegwart, "Interacting Mobile Robots on the Web", Proceedings of the 1999 IEEE International Conference on Robotics and Automation, May 1999.

Simmons, "Xavier: An Autonomous Mobile Robot on the Web", IEEE Robotics and Automation Magazine, 1999, pp. 43-48.

"Spawar Systems Center, Robart", San Diego, CA, http://web.archive.org/web/19981202205636/http://www.nosc.mil/robots/land/robart/robart.html, 1998.

Stephenson, Gary, "Dr. Robot Tested at Hopkins", Internet, Aug. 5, 2003, pp. 1-2.

Stoianovici, et al., "Robotic Tools for Minimally Invasive Urologic Surgery", Internet, Dec. 2002, pp. 1-17.

Suplee, "Mastering the Robot", The Washington Post, http://www.cs.cmu.edu-nursebotlweb/press/wash/index.html, Sep. 17, 2000, p. A01.

Telepresence Research, Inc., "Telepresence Mobile Robot System", http://www.telepresence.com/telepresence-research/Telerobot/, Feb. 20, 1995.

Urquhart, Kim, "lnTouch's robotic Companion 'beams up' healthcare experts", Medical Device Daily, vol. 7, No. 39, Feb. 27, 2003, pp. 1,4.

Weiss, et al., "Telework and video-mediated communication: Importance of real-time, interactive communication for workers with disabilities", California State University Northridge http://www.csun.edu/cod/conf/1999/proceedings/session0238.html, pp. 1-4.

West, et al., "Design of Ball Wheel Mechanisms for Omnidirectional Vehicles with Full Mobility and Invariant Kinematics", Journal of Mechanical Design, vol. 119, Jun. 1997, pp. 153-161.

Yamasaki, et al., "Applying Personal Robots and Active Interface to Video Conference Systems", Internet, 1995, pp. 243-248.

Yong, et al., "Robot task execution with telepresence using virtual reality technology", Internet, 1998, pp. 1-8.

Zamrazil, Kristie, "Telemedicine in Texas: Public Policy Concerns", House Research Organization Focus Report, Texas House of Representatives, http://www.hro.house.state.tx.us/focus/telemed.pdf, May 5, 2000, pp. 76-22.

* cited by examiner

MEDICAL TELE-ROBOTIC SYSTEM

CROSS REFERENCE TO RELATED APPLICATIONS

This application is a divisional application claiming priority to U.S. patent application Ser. No. 10/206,457, filed Jul. 25, 2002, now U.S. Pat. No. 6,925,357, issued Aug. 2, 2005; and, U.S. patent application Ser. No. 10/913,621, filed Aug. 6, 2004 now U.S. Pat. No. 7,164,970.

BACKGROUND OF THE INVENTION

1. Field of the Invention

The subject matter disclosed generally relates to the field of robotics used in the medical field.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. There have also been developed "toy" robots for home use. Such robots typically have a relatively simple movement platform and some type of speech synthesis for generating words and sounds. It would be desirable to provide a robotic system that would allow for remote patient monitoring and assistance.

BRIEF SUMMARY OF THE INVENTION

A robot that may include a camera and a monitor that are attached to a housing. The robot may also have a platform that is attached to the housing and coupled to a controller. The controller may be coupled to a broadband interface.

DETAILED DESCRIPTION

Disclosed is a robotic system that includes a remote controlled robot. The robot may include a camera, a monitor and a holonomic platform all attached to a robot housing. The robot may be controlled by a remote control station that also has a camera and a monitor. The remote control station may be linked to a base station that is wirelessly coupled to the robot. The cameras and monitors allow a care giver at the remote location to monitor and care for a patient through the robot. The holonomic platform allows the robot to move about a home or facility to locate and/or follow a patient.

Figure 1:
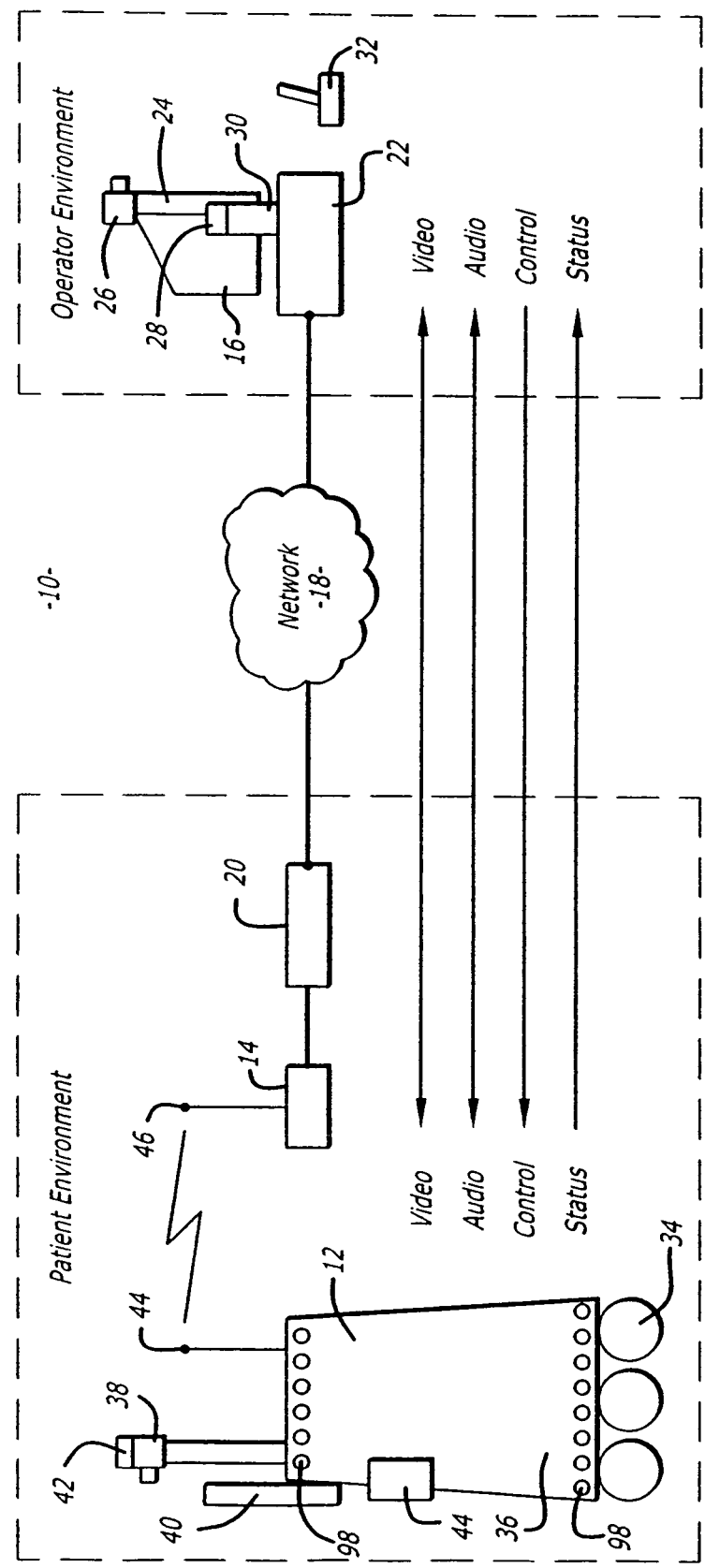
FIG. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. Additionally, although only the robot 12 is shown it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16. The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antennae 44 that is wirelessly coupled to an antennae 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
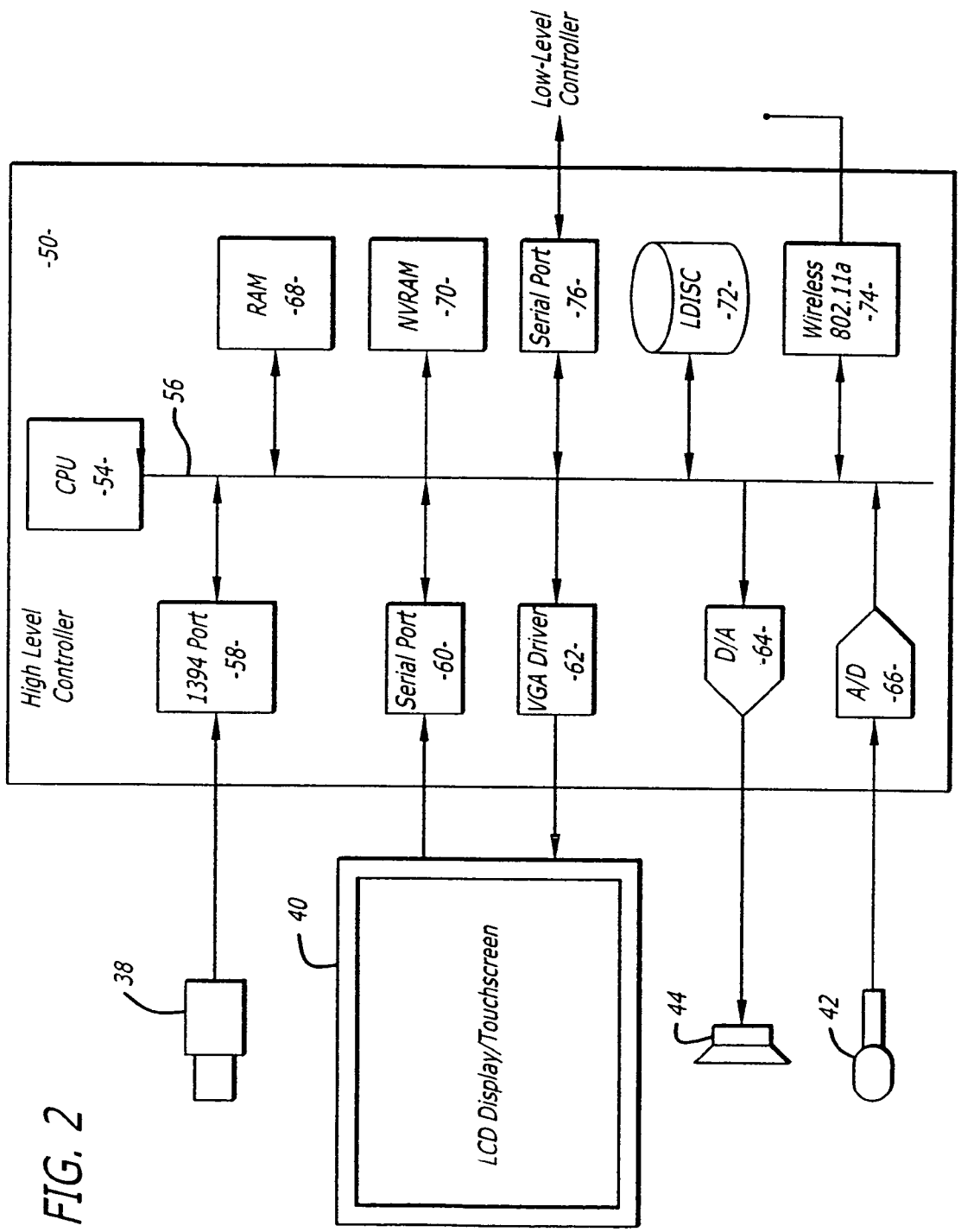
FIG. 2 is a schematic of an electrical system of a robot.
Figure 3:
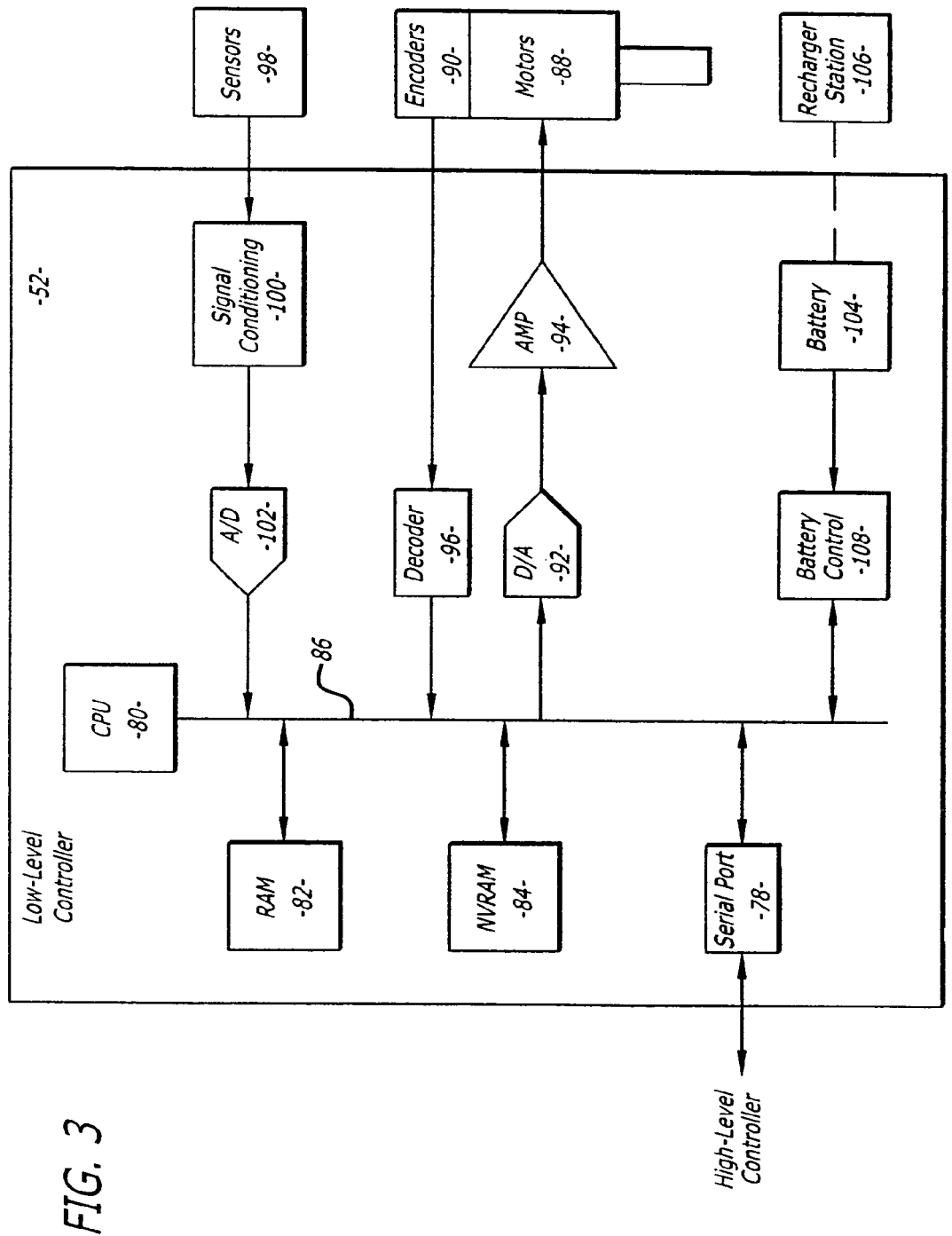
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 44 may be coupled to a wireless transceiver 74. By way of example, the transceiver 74 may transmit and receive information in accordance with IEEE 802.11a.

The controller 54 may operate with a LINUX OS operating system. The controller 54 may also operate X WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12, or to actuate an arm of the robot. The low level controller 52 may receive movement instructions from the high level controller 50. The movement instructions may be received as movement commands from the remote control station. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106.

Figure 4:
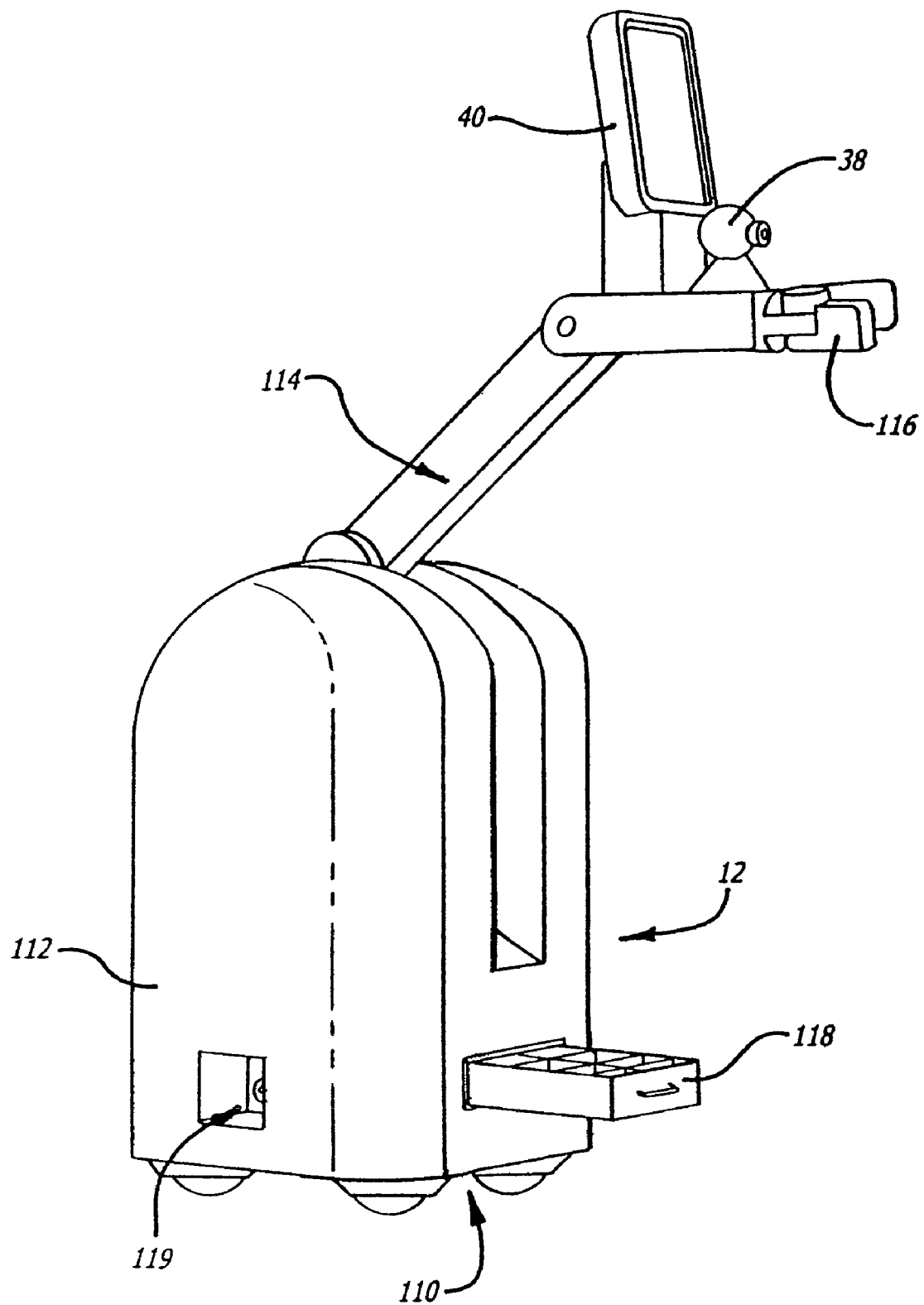
FIG. 4 is an illustration of a robot with an arm in an upward position.

FIG. 4 shows an embodiment of the robot 12. The robot 12 may include a holonomic platform 110 that is attached to a robot housing 112. The holonomic platform 110 allows the robot 12 to move in any direction. Although not shown the robot housing 112 may include bumpers.

The robot 12 may have an arm 114 that supports the camera 38 and monitor 40. The arm 114 may have two degrees of freedom so that the camera 26 and monitor 24 can be moved from an upper position shown in FIG. 4 to a lower position shown in FIG. 5. The arm 114 may have an end effector 116 such as a gripper that can grasp objects.

The robot 12 may include a drawer 118 that can automatically move between a closed position and an open position. The drawer 118 can be used to dispense drugs to a patient. For example, the drawer 118 may include a drug(s) that must be taken at a certain time. The robot 12 may be programmed so that the drawer 118 is opened at the desired time. A nurse or other health care provider may periodically "load" the drawer 118. The robot may also have a battery recharger port 119. Although drugs are described, it is to be understood that the drawer 118 could hold any item.

Figure 6:
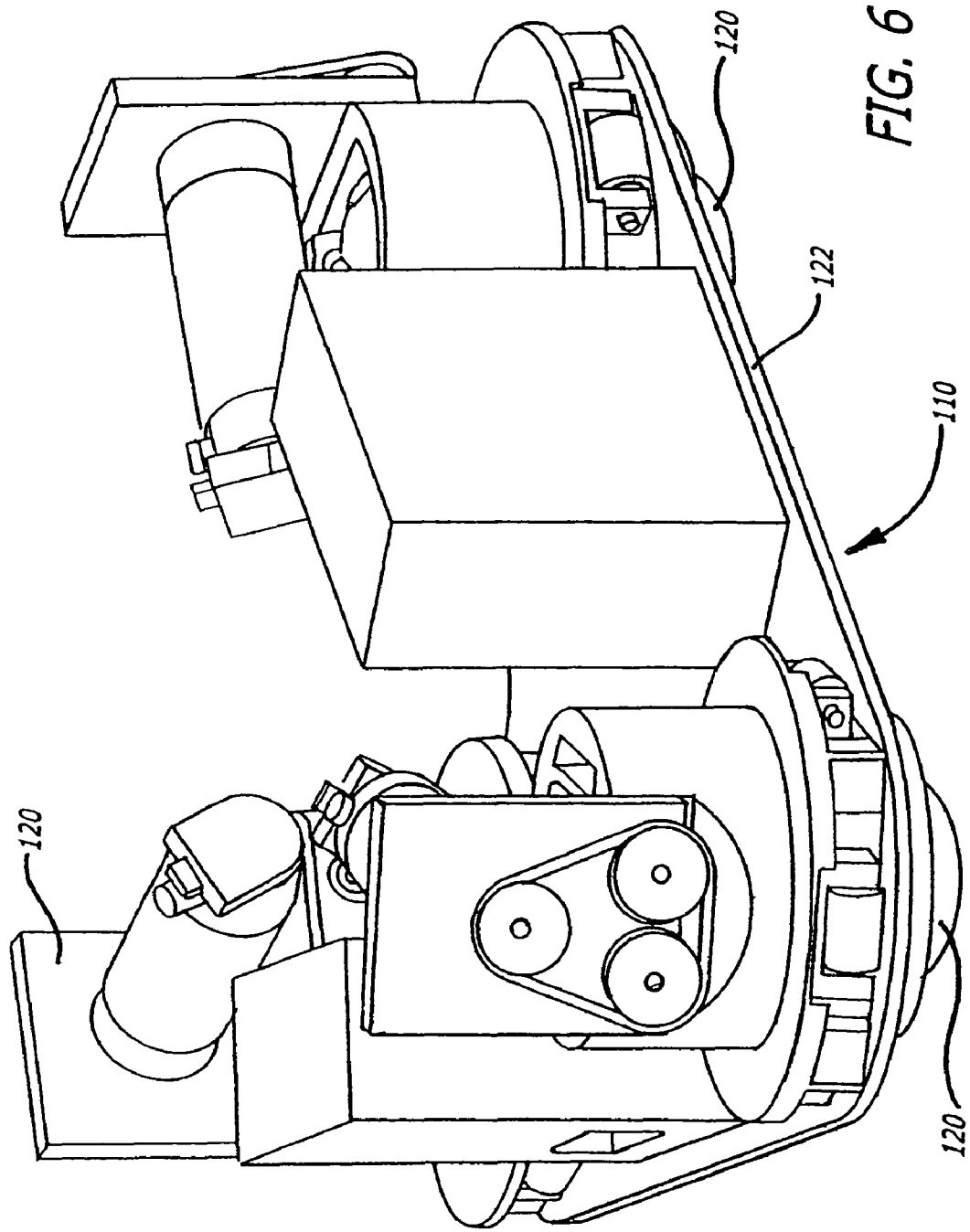
FIG. 6 is an illustration of a holonomic platform of the robot.

As shown in FIG. 6 the holonomic platform 110 may include three roller assemblies 120 that are mounted to a base plate 122. The roller assemblies 120 are typically equally spaced about the platform 110 and allow for movement in any direction.

Figure 7:
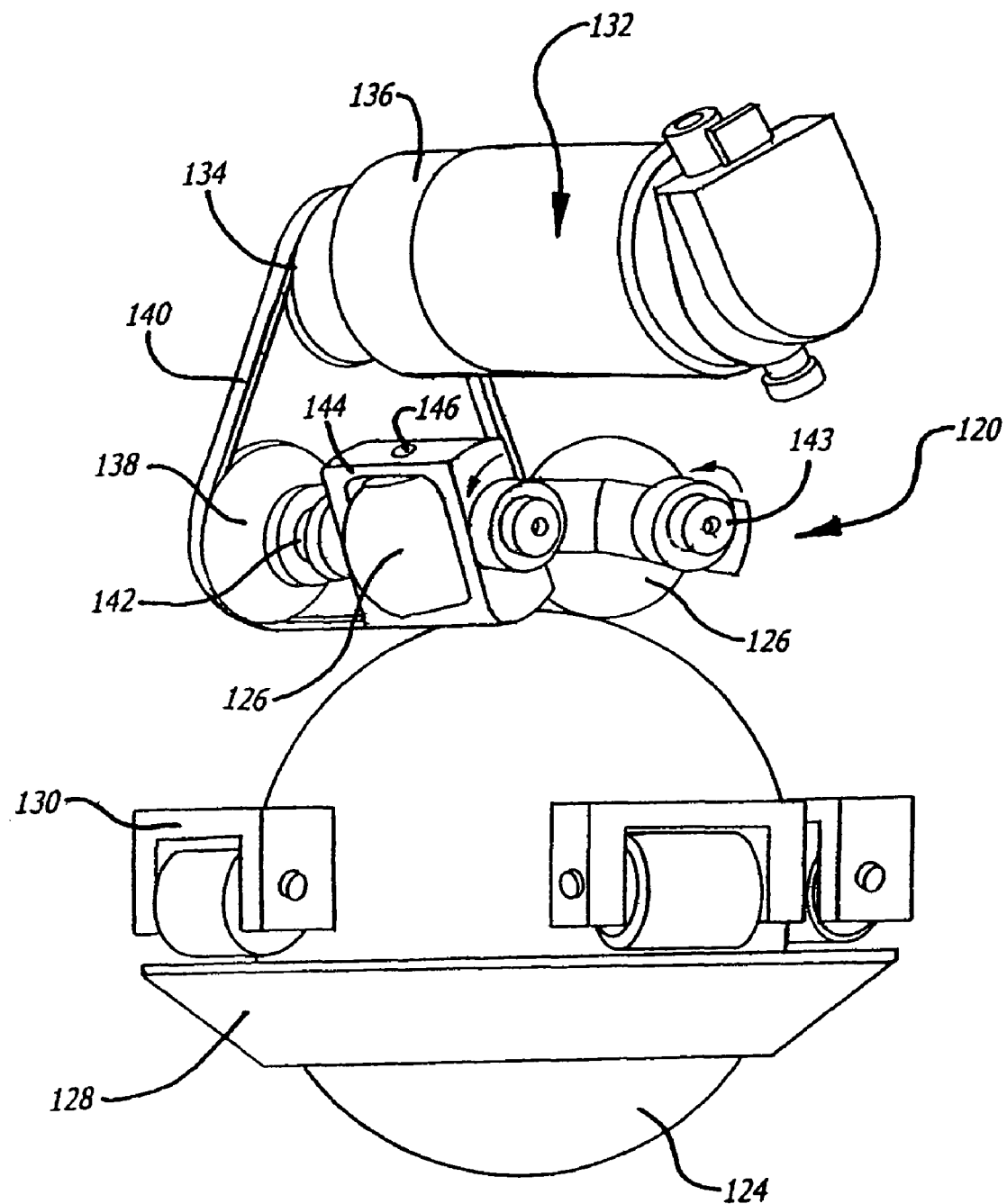
FIG. 7 is an illustration of a roller assembly of the holonomic platform.

FIG. 7 shows an embodiment of a roller assembly 120. Each assembly 120 may include a drive ball 124 that is driven by a pair of transmission rollers 126. The assembly 120 includes a retainer ring 128 and a plurality of bushings 130 that allow the ball 124 to rotate in an x and y direction but prevents movement in a z direction.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are attached to drive pins 142 that are attached to a bracket 144. The transmission rollers 126 are attached to a bearing bracket 144 by a roller pin 146.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The drive balls 126 are out of phase so that one of the balls 126 is always in contact with ball 124. The roller pin 146 and bracket 144 allow the transmission rollers 126 to freely spin and allow orthoganal directional passive movement when one of the other roller assemblies 120 is driving and moving the robot 12.

Figure 8:
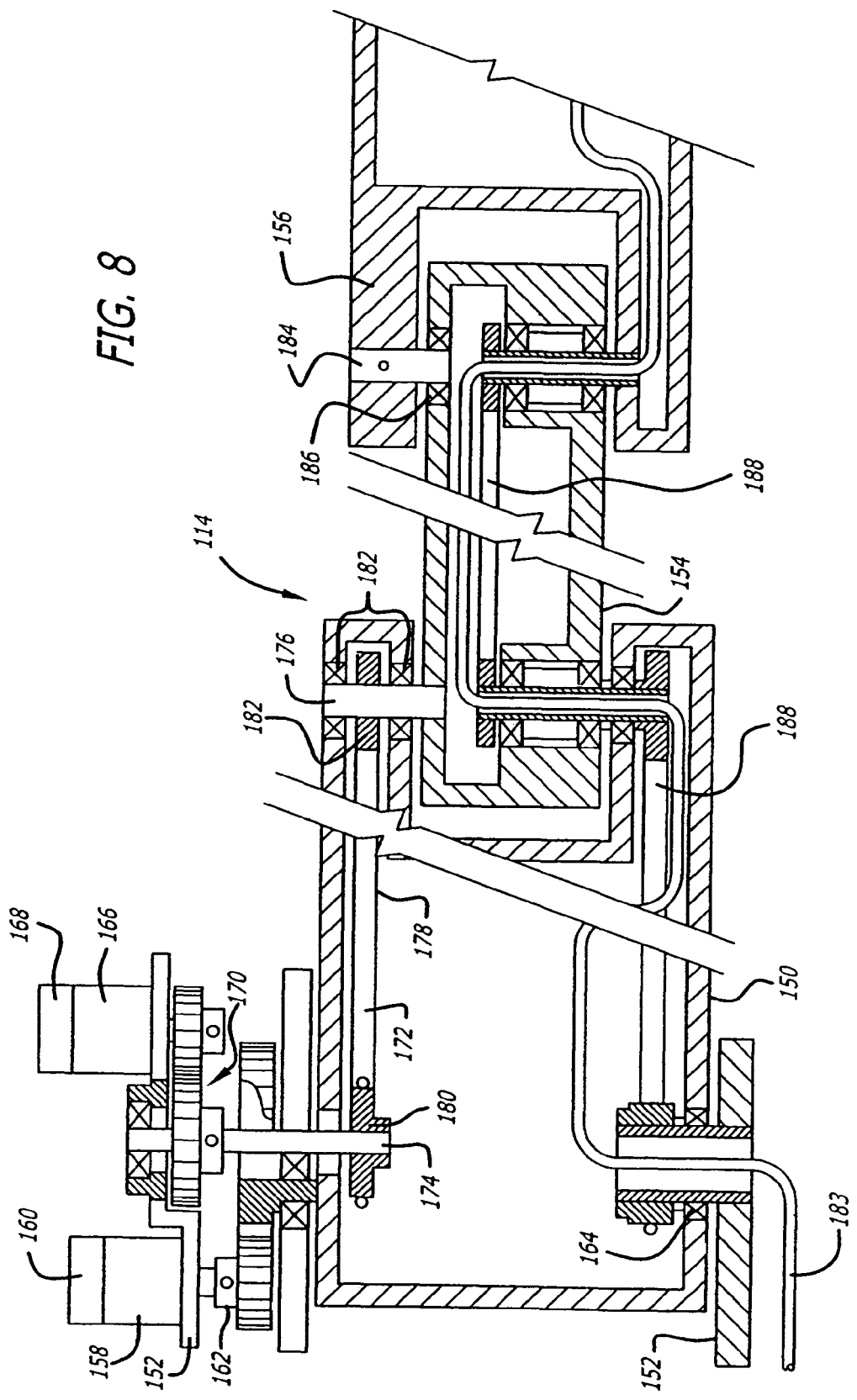
FIG. 8 is an illustration of an arm assembly of the robot.
Figure 9:
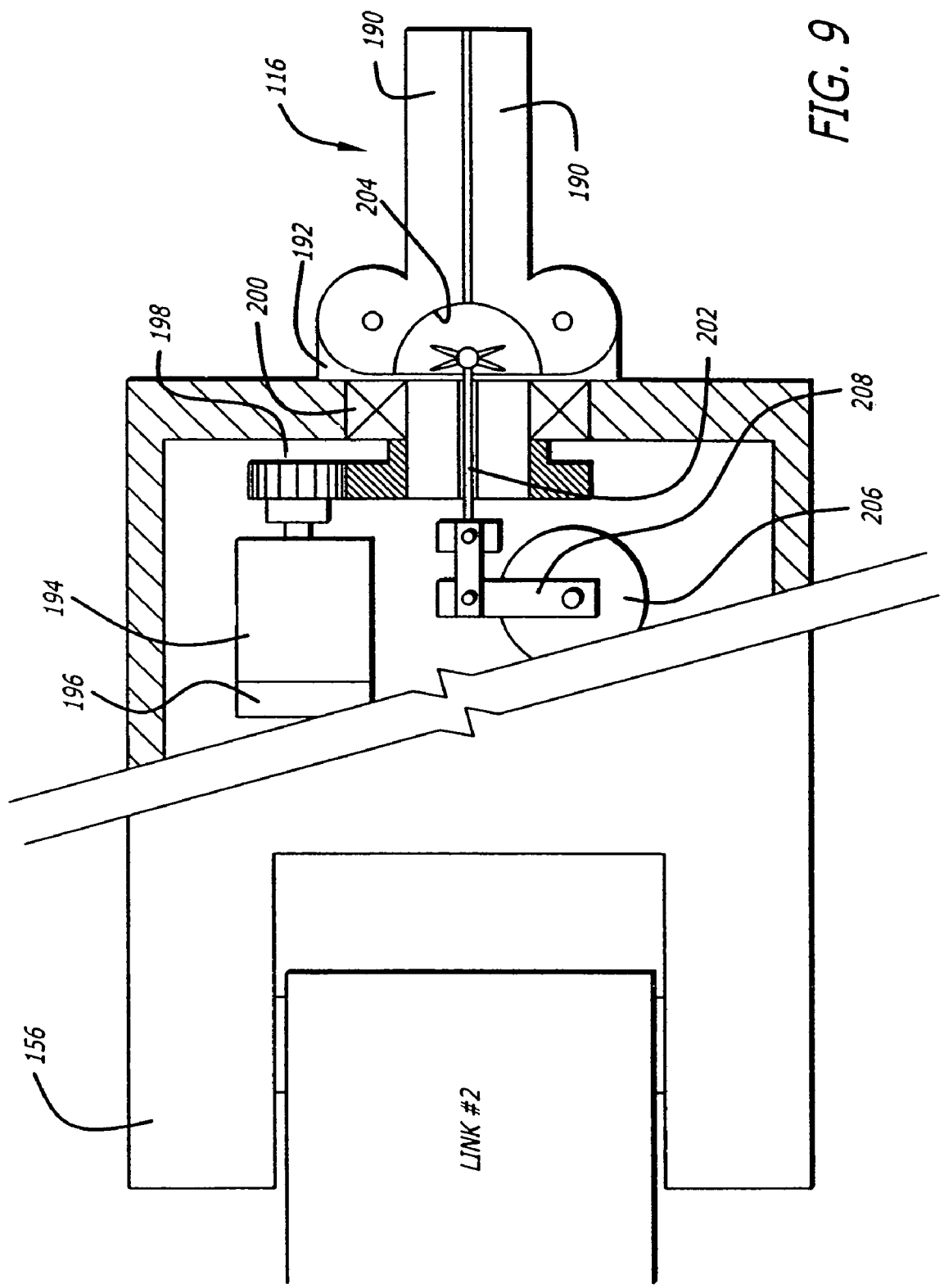
FIG. 9 is an illustration of a gripper assembly of the arm.

FIGS. 8 and 9 show an embodiment of the arm 114. The arm 114 may include a first linkage 150 that is pivotally mounted to a fixed plate 152 of the robot housing 12. The arm 114 may also include a second linkage 154 that is pivotally connected to the first linkage 150 and a third linkage 156 that is pivotally connected to the second linkage 154.

The first linkage 150 may be coupled to a first motor 158 and motor encoder 160 by a gear assembly 162. Rotation of the motor 158 will cause a corresponding pivotal movement of the linkage 150 and arm 114. The linkage 150 may be coupled to the fixed plate 152 by a bearing 164.

The second linkage 154 may be coupled to a second motor 166 and encoder 168 by a gear assembly 170 and a pulley assembly 172. The pulley assembly 172 may be connected to the gear assembly 170 by a pin 174 that extends through the gear assembly 162 of the first motor 158. The second linkage 154 may be attached to a pin 176 that can spin relative to the first linkage 150. The pulley assembly 172 may have a belt 178 that couples a pair of pulleys 180 and 182 that are attached to pins 174 and 176, respectively. Pin 176 may be coupled to the first linkage 150 by bearings 182. The arm 114 is configured to allow wires 183 to be internally routed through the linkages 150, 154 and 156.

Figure 5:
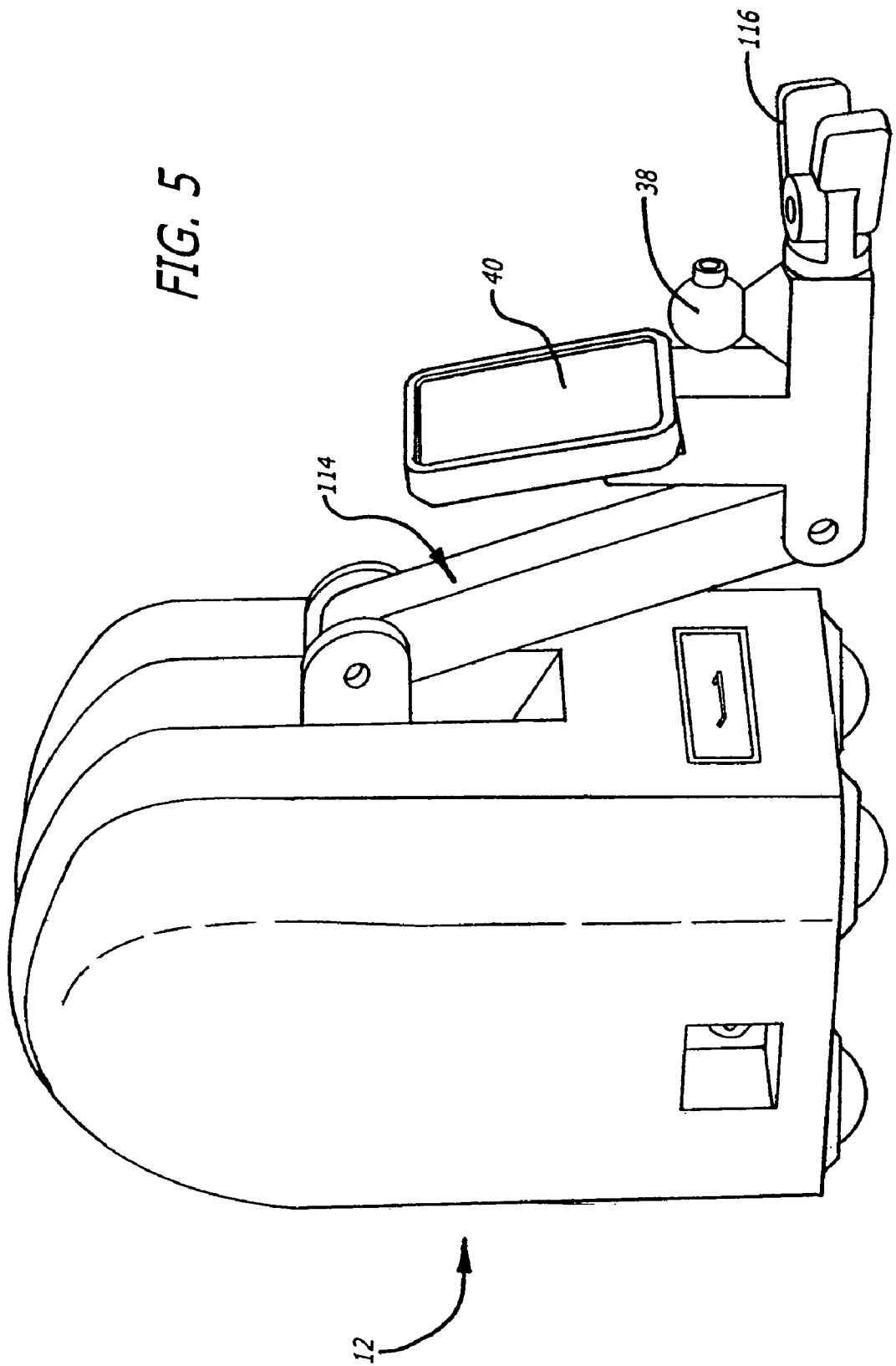
FIG. 5 is an illustration of the robot with the arm in a lower position.

The third linkage 156 may be connected to a pin 184 that can spin relative to the second linkage 154. The pin 184 may be coupled to the second linkage 154 by a bearing assembly 186. The third linkage 156 may be structurally coupled to the first linkage 150 by a pair of pulley assemblies 188. The pulley assembly 188 insures a horizontal position of the third linkage 156 no matter what position the first 150 and second 154 linkages are in. As shown in FIGS. 4 and 5 the third linkage 156 is always in a horizontal position. This insures that the camera 26 is always in the same orientation, thus reducing the possibility of disorientation at the remote control station when viewing the patient.

The gripper 116 is attached to the third linkage 156. The gripper 116 may include a pair of fingers 190 that are pivotally attached to a base plate 192. The fingers 190 are coupled to a motor 194 and encoder 196 by a gear assembly 198. The base plate 192 is coupled to the third linkage 156 by a bearing assembly 200. The motor 194 can spin the base plate 192 and fingers 192 relative to the third linkage 156.

The gripper 116 may further have a push rod 202 that can engage cam surfaces 204 of the fingers 190 to move the gripper fingers 190 between open and closed positions. The push rod 202 may be coupled to a motor 206 and encoder (not shown) by a linkage assembly 208. Actuation of the motor 206 will translate the push rod 202 and move the fingers 190. The motor 206 may have a force sensor that provides force feedback back to the remote control station. The input device of the remote control station may have a force feedback mechanism so that the user feels the force being exerted onto the gripper fingers 190.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control station allow for teleconferencing between the patient and the person at the remote station.

The robot 12 can be maneuvered through the home or facility by manipulating the input device 32 at the remote station 16. The robot 12 may also have autonomous movement. For example, the robot 12 may be programmed to automatically move to a patients room at a certain time to dispense drugs in the drawer 118 without input from the remote station 16. The robot 12 can be programmed to monitor and/or assist a patient 24 hours a day, 7 days a week. Such a monitoring capability is enhanced by the autonomous recharging function of the robot.

The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| | Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| | Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| | Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 10:
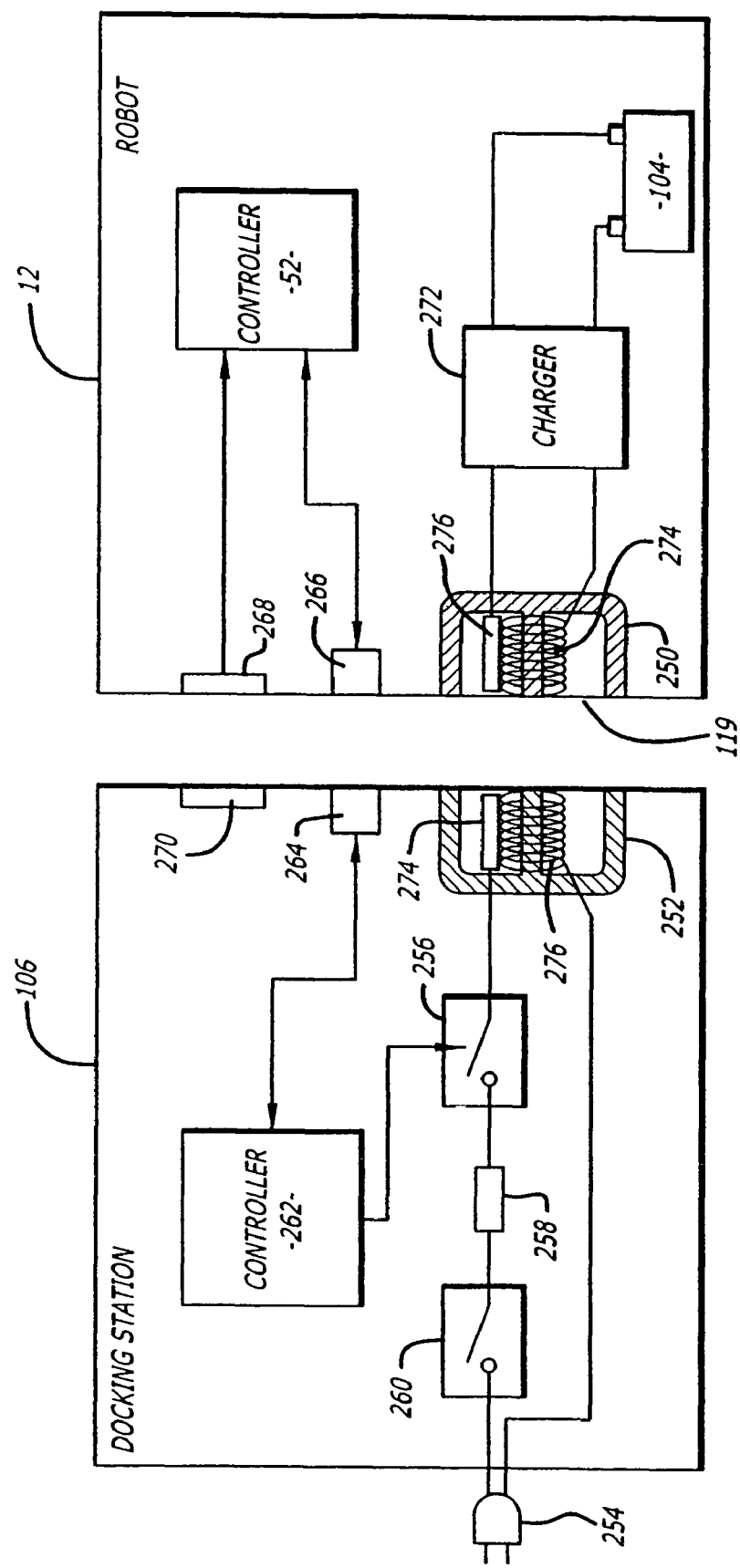
FIG. 10 is a schematic of a battery recharger for the robot.

FIG. 10 shows an embodiment of a battery recharger. The robot port 119 may include a secondary winding 250 that is magnetically coupled to a primary winding 252 of the battery recharger station 106. The primary winding 252 is coupled to an electrical outlet plug 254 by a relay circuit 256, a fuse 258 and a switch 260. The relay 256 is controlled by a recharger controller 262.

The recharger controller 262 is connected to a recharger infrared (IR) transceiver 264. The recharger IR transceiver 264 is coupled to a robot IR transceiver 266. The robot IR transceiver 266 is connected to the low level controller 52. The robot 10 may also have an alignment sensor 268 that can sense a target 270 on the station 106. By way of example, the sensor 268 may include an optical emitter and receiver that detects a light beam reflected from the target 270. The controller 52 may also sense a current flow into the battery 104 to determine whether the robot 12 is aligned with the docking station 106.

The secondary windings 250 are connected to the battery 104 by a charger circuit 272. The secondary 250 and primary 252 windings may each have wires 274 wrapped about a magnetic core 276. The station 106 may also have an oscillator/chopper circuit (not shown) to increase the voltage magnetically transferred to the secondary winding 250.

In operation, the robot 10 is moved to the battery recharger station 106 either autonomously, or by user control. The robot 10 is moved until the sensor 268 is aligned with the target 270. The low level controller 52 then sends a command to the recharger controller 262 through the transceivers 264 and 266. The recharger controller 262 then closes the relay 256 wherein power is transferred to the battery 104 through the windings 250 and 252. When the battery 104 is recharged, or the battery recharging process is interrupted by the user, the low level controller 52 transmits a command to the recharger controller 262 to open the relay 256. The robot 10 then moves away from the recharging station 106.

Figure 11:
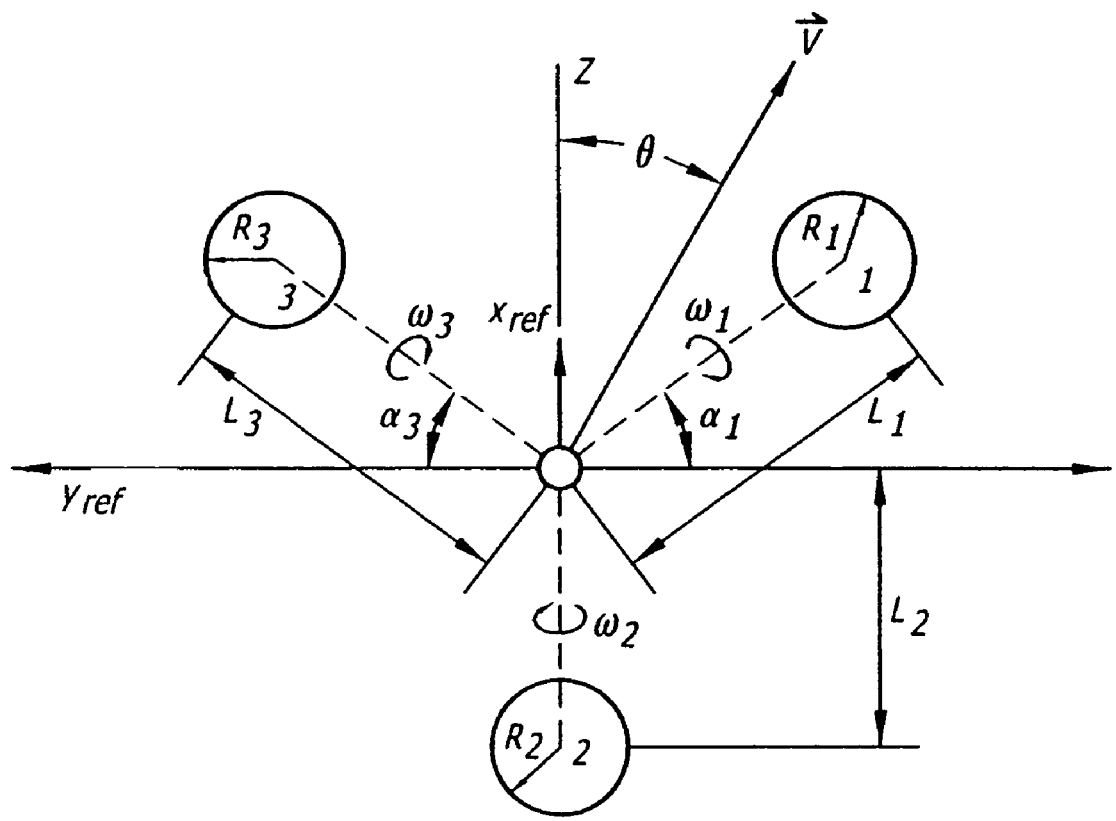
FIG. 11 is a Vector Diagram that may be used to compute movement of the robot.

FIG. 11 shows a vector diagram that can be used to compute movement of the robot with the following equations:

$$w_1 = \frac{|V|}{R_1}(\mathrm{Sin}\, \alpha_1\, \mathrm{Sin}\theta - \mathrm{Cos}\, \alpha_1\, \mathrm{Cos}\theta) + \frac{\Psi L_1}{R_1} \quad (1)$$

$$w_2 = \frac{|V|}{R_2}\mathrm{Sin}\theta + \frac{\Psi L_2}{R_2} \quad (2)$$

$$w_3 = \frac{|V|}{R_3}(\mathrm{Sin}\, \alpha_2\, \mathrm{Sin}\theta + \mathrm{Cos}\, \alpha_2\, \mathrm{Cos}\theta) + \frac{\Psi L_3}{R_3} \quad (3)$$

where,
$w_2$=is the angular velocity of a first roller.
$w_2$=is the angular velocity of a second roller.
$w_3$=is the angular velocity of a third roller.
V=is the input linear velocity for the robot which components $V_x$=|V|cos θ and $-V_y$=|V|sin θ.
ψ=is the input angular velocity for the robot.

The values $w_1$, $w_2$ and $w_3$ can be obtained by solving for the inverse of the following matrix:

$$A = \begin{bmatrix} -\dfrac{\cos\alpha_1}{R_1} & \dfrac{\sin\alpha_1}{R_1} & \dfrac{L_1}{R_1} \\ 0 & -\dfrac{1}{R_2} & \dfrac{L_2}{R_2} \\ \dfrac{\cos\alpha_3}{R_3} & \dfrac{\sin\alpha_3}{R_3} & \dfrac{L_3}{R_3} \end{bmatrix}$$

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for interacting with a patient, comprising:
    transmitting commands from a control station to a robot that has a camera, a monitor, a speaker and a microphone;
    moving the robot in response to the commands;
    capturing a still image of a patient with the robot camera;
    capturing a live video image of the patient with the robot camera, the still image is not a part of the live video image; displaying simultaneously the still image of the patient and the live video image of the patient on a monitor of control station capturing an image of an operator with a control station camera, transmitting the captured operator image to the robot and displaying the transmitted captured operator image on a robot monitor;
    transmitting a voice message from the control station to the robot; and,
    transmitting a patient voice message from the robot to the control station.

2. The method of claim 1, wherein the still image of the patient is stored in the robot.

3. The method of claim 1, wherein the robot moves across a surface.

* * * * *